US009606086B2

(12) United States Patent
Ding et al.

(10) Patent No.: US 9,606,086 B2
(45) Date of Patent: Mar. 28, 2017

(54) HIGH-EFFICIENCY SEPARATION AND MANIPULATION OF PARTICLES AND CELLS IN MICROFLUIDIC DEVICE USING SURFACE ACOUSTIC WAVES AT AN OBLIQUE ANGLE

(71) Applicant: The Penn State Research Foundation, University Park, PA (US)

(72) Inventors: Xiaoyun Ding, State College, PA (US); Tony Jun Huang, State College, PA (US)

(73) Assignee: The Penn State Research Foundation, University Park, PA (US)

( * ) Notice: Subject to any disclaimer, the term of this patent is extended or adjusted under 35 U.S.C. 154(b) by 656 days.

(21) Appl. No.: 13/955,709

(22) Filed: Jul. 31, 2013

(65) Prior Publication Data

US 2014/0033808 A1  Feb. 6, 2014

Related U.S. Application Data

(60) Provisional application No. 61/678,214, filed on Aug. 1, 2012.

(51) Int. Cl.
  *G01N 29/02* (2006.01)
  *B01L 3/00* (2006.01)
  (Continued)

(52) U.S. Cl.
  CPC ........ *G01N 29/02* (2013.01); *B01L 3/502761* (2013.01); *C12M 47/04* (2013.01);
  (Continued)

(58) Field of Classification Search
  CPC ................ G01N 29/02; G01N 29/022; G01N 2291/02466; G01N 2291/02416;
  (Continued)

(56) References Cited

U.S. PATENT DOCUMENTS 4,735,097 A * 4/1988 Lynnworth ............. G01F 1/662
                                                        73/290 V
5,369,998 A * 12/1994 Sowerby .................. G01F 1/66
                                                        73/861.04
(Continued)

FOREIGN PATENT DOCUMENTS

EP  2145687     1/2010
RU  2243630     12/2004
(Continued)

OTHER PUBLICATIONS

International Search Report and Written Opinon for corresponding PCT Application No. PCT/US2013/052482 issued Nov. 21, 2013.
(Continued)

*Primary Examiner* — John Fitzgerald
*Assistant Examiner* — Marrit Eyassu
(74) *Attorney, Agent, or Firm* — McNees Wallace & Nurick LLC (57) ABSTRACT

An apparatus for manipulating particles within a fluid sample includes a substrate having a substrate surface. A surface acoustic wave (SAW) generator generates a SAW within a SAW region of the substrate surface. The SAW has an SAW direction aligned with a pressure node. A channel is configured to receive the fluid sample and the fluid sample has a flow direction which is at an oblique angle to the SAW direction.

17 Claims, 8 Drawing Sheets

(51) Int. Cl.
*C12M 1/00* (2006.01)
*G01N 29/22* (2006.01)
*G01N 15/14* (2006.01)
*G01N 15/00* (2006.01)
*G01N 15/10* (2006.01)

(52) U.S. Cl.
CPC ....... *G01N 15/1459* (2013.01); *G01N 29/222* (2013.01); *B01L 2200/0636* (2013.01); *B01L 2200/0652* (2013.01); *B01L 2300/0864* (2013.01); *B01L 2400/0436* (2013.01); *G01N 2015/0019* (2013.01); *G01N 2015/1006* (2013.01); *G01N 2291/02466* (2013.01); *G01N 2291/0423* (2013.01)

(58) Field of Classification Search
CPC ........... G01N 29/032; G01N 2015/142; G01N 15/02; G01N 29/036; G01N 29/024; G01N 29/222; G01N 2015/0019; G01N 2291/0423; C12M 47/04; B01L 3/502761; B01L 2400/0436
USPC ........... 73/61.75, 61.71, 570.5, 61.49, 61.73, 73/61.79
See application file for complete search history.

(56) References Cited

U.S. PATENT DOCUMENTS

| | | | |
|---|---|---|---|
| 5,633,552 A | 5/1997 | Lee et al. | |
| 6,168,948 B1 | 1/2001 | Anderson et al. | |
| 6,348,968 B2 * | 2/2002 | Autrey | 356/246 |
| 6,537,498 B1 | 3/2003 | Lewis et al. | |
| 6,669,454 B2 | 12/2003 | Lal et al. | |
| 7,601,267 B2 | 10/2009 | Haake et al. | |
| 7,601,287 B2 | 10/2009 | Adair et al. | |
| 7,942,568 B1 * | 5/2011 | Branch | B01F 13/0059 366/127 |
| 8,573,060 B2 | 11/2013 | Huang et al. | |
| 2001/0055529 A1 | 12/2001 | Wixforth | |
| 2004/0069717 A1 | 4/2004 | Laurell et al. | |
| 2005/0241935 A1 | 11/2005 | Lewis et al. | |
| 2006/0024206 A1 | 2/2006 | Sinha et al. | |
| 2008/0098818 A1 * | 5/2008 | Fernald | G01F 1/7082 73/622 |
| 2008/0181827 A1 | 7/2008 | Bassler et al. | |
| 2008/0229831 A1 | 9/2008 | Serban et al. | |
| 2008/0245745 A1 | 10/2008 | Ward et al. | |
| 2008/0302732 A1 | 12/2008 | Soh et al. | |
| 2009/0066936 A1 | 3/2009 | Huang et al. | |
| 2009/0158822 A1 * | 6/2009 | Sun | G01N 15/06 73/61.75 |
| 2009/0158823 A1 | 6/2009 | Kaduchak et al. | |
| 2009/0162887 A1 | 6/2009 | Kaduchak et al. | |
| 2009/0226994 A1 | 9/2009 | Lemor et al. | |
| 2010/0078384 A1 * | 4/2010 | Yang | B01D 21/283 210/645 |
| 2010/0126922 A1 * | 5/2010 | Takahashi | B01D 21/283 210/201 |
| 2010/0139377 A1 * | 6/2010 | Huang | B01L 3/502761 73/61.75 |
| 2010/0200092 A1 | 8/2010 | Beltram et al. | |
| 2010/0304501 A1 | 12/2010 | Lee et al. | |
| 2011/0154890 A1 * | 6/2011 | Holm | B01D 21/283 73/61.75 |
| 2012/0088295 A1 | 4/2012 | Yasuda et al. | |
| 2012/0160746 A1 * | 6/2012 | Thorslund | B01L 3/502761 209/552 |
| 2013/0043170 A1 * | 2/2013 | Rose | B01D 21/283 209/659 |
| 2014/0008307 A1 * | 1/2014 | Guldiken | B01L 3/502761 210/748.05 |
| 2015/0192546 A1 * | 7/2015 | Weitz | G01N 29/222 137/13 |

FOREIGN PATENT DOCUMENTS

| | | |
|---|---|---|
| RU | 2253888 C2 | 6/2005 |
| WO | WO-03089158 | 10/2003 |
| WO | WO-2007128045 | 11/2007 |
| WO | WO-2007128046 A1 | 11/2007 |
| WO | WO-2008083138 A1 | 7/2008 |
| WO | WO-2008118740 A2 | 10/2008 |

OTHER PUBLICATIONS

Nilsson, et al., Acoustic control of suspended particles in micro fluidic chips, Lab on a Chip, 4:131-135, 2004.

Wang, et al., Single-molecule tracing on a fluidic microchip for quantitative detection of low-abundance nucleic acids, Journal of the American Chemical Society, 127:5354-5359, 2005.

Wang, et al., Dielectrophoresis switching with vertical sidewall electrodes for microfluidic flow cytometry, Lab on a Chip, 7:1114-1120, 2007.

Wiklund, et al., Ultrasonic standing wave manipulation technology integrated into dielectrophoretic chip, Lab on a Chip, 6:1537-1544, 2006.

Shi, et al., Focusing microparticles in a microfluidic channel with standing surface acoustic waves (SSAW), Lab on a Chip, 8:221-223, 2008.

Shi, et al., Acoustic tweezers: patterning cells and microparticles using standing surface acoustic waves (SSAW), Lab on a Chip, 9:2890-2895, 2009.

Mao, et al., Focusing fluids and light: enabling technologies for single-particles detection in the micro/nanoscale, IEEE Nanotechnology Magazine, 2:22-27, 2008.

Mao, et al., "Microfluidic drifting"—implementing three-dimensional hydrodynamic focusing with a single-layer planar microfluidic device, Lab on a Chip, 7:1260-1262, 2007.

Mao, et al., Single-layer planar on-chip flow cytometer using microfluidic drifting based three-dimensional (3D) hydrodynamic focusing, Lab on a Chip, 9:1583-1589, 2009.

Wood, C.D. et al., "Alignment of particles in microfluidic systems using standing surface acoustic waves," Applied Physics Letters, 2008, vol. 92, 044104 (Published online Jan. 30, 2008).

European Search Report, 52 pages, Jul. 4, 2016.

L. Johansson et al., "Surface Acoustic Wave Induced Particle Manipulation in a PDMS Channel-Principle Concepts for Continuous Flow Applications", Biomed Microdevices, (2012) 14:279-289.

* cited by examiner

HIGH-EFFICIENCY SEPARATION AND MANIPULATION OF PARTICLES AND CELLS IN MICROFLUIDIC DEVICE USING SURFACE ACOUSTIC WAVES AT AN OBLIQUE ANGLE

CROSS-REFERENCE TO RELATED APPLICATION

This patent application claims priority from U.S. provisional patent application Ser. No. 61/678,214, filed Aug. 1, 2012, the content of which is incorporated herein in its entirety.

STATEMENT OF GOVERNMENT SUPPORT

This invention was made with government support under Grant No. OD007209, awarded by the National Institutes of Health, and under Grant No. ECCS-0801922 awarded by the National Science Foundation. The government has certain rights in the invention.

FIELD OF THE INVENTION

The invention relates to methods and apparatus for particle or cell manipulation, such as separation and focusing, and particle or cell detection and characterization.

BACKGROUND OF THE INVENTION

Efficient separation of suspended particles and cells is essential to many fundamental biomedical studies such as cancer cell detection and drug screening. The most popular methods for cell separation in the life science laboratory so far are the centrifugal methods, which are capable of separating cells with differences in size and density. Another industrial and clinical standard for high quality cell separation is a FACS (fluorescence activated cell sorter). The FACS technology is performed in a sheath flow mode where cells are focused in the center of buffer and then pass through a laser beam for high speed and precise optical detection. The cells can be separated by a downstream electric field triggered by the optical signal. In the past years, fundamental advances in the lab-on-a-chip technologies have driven development of new approaches to cell separation. Examples include magnetic, hydrodynamic, optical lattice, electrophoresis/dielectrophoretic (DEP), and acoustic methods.

The magnetic method starts with labeling cells of interest with magnetic markers. Then an external magnetic field is applied to the sample, leading to the separation of labeled cells from the rest. The labeling step required for magnetic methods usually increases cost and processing time, and may also have a negative effect on the cells of interest. The hydrodynamic methods usually involve high flow speed (inertial force based method) or asymmetric obstacles inside the channel (deterministic lateral displacement). These methods permit continuous operation without requiring additional labeling or external forces. However, the channel obstacles in the channel may exert high mechanical stress on cells and lead to low throughput. The optical lattice method provides a unique separation approach which can separate particles with different optical properties. However, this approach has two potential shortcomings: 1) the potential laser-induced heating, the formation of singlet oxygen, and multiphoton absorption in biological materials may cause physiological damage to cells and other biological objects; and 2) the method relies on complex, potentially expensive optical setups that are difficult to maintain and miniaturize. Electrophoresis/dielectrophoresis based methods are strictly dependent on particle polarizibility and medium conductivity, and utilize electrical forces that may adversely affect cell physiology due to current-induced heating and/or direct electric-field interaction.

Acoustic-based particle manipulation methods present excellent alternatives. Compared to their optical, electrical, or magnetic counterparts, acoustic-based methods are relatively non-invasive to biological objects and work for most microparticles regardless of their optical, electrical, or magnetic properties. The well developed bulk acoustic wave (BAW) acoustophoresis has demonstrated the separation of cells based on size and density in microfluidic chips without any labeling on the target particles or cells. This BAW method, however, requires a channel material with excellent acoustic reflection properties (such as silicon and glass). The widely used soft polymer materials in microfluidic applications, such as PDMS, usually do not have those properties. Moreover, the transducer to generate BAW is bulky and hinders the system integration and miniaturization.

SUMMARY OF THE INVENTION

The present invention provides a unique design based on a surface acoustic wave method. Some versions demonstrate a high separation efficiency with separation efficiency of 98% or higher. Cell viability, proliferation, and apoptosis tests were carried out to confirm the excellent biocompatibility of this device.

An example apparatus for separating particles within a fluid sample comprises a substrate, one or more transducers for generating a surface acoustic wave (SAW) in the substrate, and a channel configured to receive a fluid sample including one or more species of particle. The fluid sample may be a sample fluid flow, and the sample fluid flow may have a focused, separated, or otherwise sorted particle stream after passing through the particle manipulation portion of the channel. The channel direction or flow direction is at an oblique angle to the direction of the SAWs. The SAWs may be standing surface acoustic waves (SSAWs)

Examples of the present invention provide novel methods and apparatus for high-efficiency separation of micro/nano particles and cells using angled or tilted surface acoustic waves on a single-layer planar microfluidic device fabricated using standard soft-lithography techniques. Systems include a low cost, high efficiency, and portable separation system for many applications such as blood/cell/particle separation, cells/particles medium exchange, and cells/particles enrichment.

A channel has a particle manipulation portion where the channel is proximate a SAW region of the substrate, for example extending over the SAW region. The SAW region can be defined using a patterned material on the substrate. The channel may be provided by a formed element, such as a molded polymer formed element, adjacent the substrate. The particle manipulation portion of the channel provides particle manipulation within the fluid sample when a surface acoustic wave is generated. The fluid sample may comprise particles suspended in a liquid, such as an aqueous medium.

In some examples, the substrate is a piezoelectric substrate, and the SAW is generated using a transducer supported by the substrate. A standing surface acoustic wave (SSAW) may be generated using a pair of surface acoustic wave generators (SAW generators), which may each be an interdigitated transducer (IDT). The SAW generators may be spaced apart on the substrate, and the SAW region of the substrate is located where SAWs interact on the surface. In some examples, a pair of SAW generators is used, and the particle manipulation region of the channel is located between the SAW generators, e.g. mechanically coupled to a SAW region of the substrate so that the SAW generates pressure forces within the fluid sample.

Example apparatus include microfluidic devices, the channel being a microchannel having at least one cross-sectional dimension (such as width or height) less than 10 mm, or less than 1 mm for some versions, for example between 1 micron and 500 microns, and the particles may be microparticles such as cells, biomolecules, polymer beads, blood components such as red and white blood cells, platelets, proteins, and the like.

An apparatus may be a particle characterization apparatus further including a particle characterization device, the particle characterization device characterizing the manipulated particles. Particle characterization may include counting, sorting, detecting (including selective detection of one or more particle species), or otherwise characterizing particles, and may include diagnosis of a human disorder based on the presence or properties of a biological fluid component. Examples include blood, saliva, urine, and other biological fluid characterization including manipulation of particles within the biological fluid. A particle characterization apparatus may include a radiation source providing a radiation beam incident on the manipulated particles, and/or a sensor receiving radiation scattered or otherwise obtained from the particles. Example particle characterization apparatus include a cytometer (such as a flow cytometer), fluorescence particle detector, fluorescence spectrometer, fluorescence-activated particle sorter, other particle sorter, particle counter, fluorescent spectrometer, biomarker detector, or genetic analyzer. Particles may be cells (e.g. human cells), biomolecules, other bioparticles, or any other type of particle of interest.

An example method of particle manipulation within a fluid sample including the particles comprises introducing the fluid sample to a channel proximate a substrate, and generating a SAW or SSAW on the substrate at an oblique angle to the channel direction. A SAW is an acoustic wave propagating along the surface of the substrate, and the surface may also be in contact with a fluid sample. The SAWs may interact to form a SSAW. The term acoustic does not limit the frequency of the SAW, which may greater than 1 GHz. Manipulated particles may be particles within a region of enhanced particle concentration within a liquid.

The SAW induces pressure forces within the fluid so as to focus the particles within the fluid sample. The sample flow may be directed along a flow channel, the flow channel being supported by the substrate in which the SAW is generated. A SAW may be used to obtain three-dimensional manipulation of the particles within the sample flow, the particles being manipulated in directions both parallel and normal to the substrate.

A novel on-chip micro/nano particle manipulation technique was developed using standing surface acoustic waves (SSAWs). Example methods and apparatus are efficient, simple, fast, dilution-free, and applicable to virtually any type of particle, including both charged and uncharged microparticles. Example methods can be used with flow cytometry, cell sorting/counting, on-chip cell manipulation, tissue engineering, regenerative medicine, non-human animal diagnosis, and many other applications.

An example apparatus, such as a microfluidic device, receives a sample flow including particles. The apparatus comprises a substrate, a channel (such as a flow channel) into which the sample is introduced, and one or more surface acoustic wave (SAW) generators. A SAW generator may be an interdigitated transducer (IDT, sometimes termed an interdigital transducer) comprising interdigitated comb-shaped electrodes on a piezoelectric substrate. The channel may pass between a pair of IDTs. The IDTs and channel may both be supported by the same piezoelectric substrate. The SAW generators may be operated to produce a SAW or SSAW in a portion of the substrate proximate (possibly immediately adjacent to) the manipulation portion of the flow channel. For example, a flow channel may be supported by the substrate, e.g. formed by a structure comprising a polymer or other material bonded to the substrate.

The flow channel has a particle manipulation region located on a portion of the substrate in which the SAW exists. For example, the flow channel may pass over a portion of the substrate having standing surface acoustic waves (SSAWs), the particles being manipulated within the flow channel by the effects of the SSAW. The substrate may be a generally planar substrate, for example a ferroelectric and/or piezoelectric substrate. A surface acoustic wave generator may comprise interdigitated electrodes supported by a ferroelectric or piezoelectric substrate. Two or more SAW generators may be used to generate a SSAW in the substrate, e.g. using interference effects between SAWs.

A method of manipulating particles within a sample, such as focusing, separating, or sorting, which may be a method of three-dimensional particle manipulation, includes producing a standing surface acoustic wave (SSAW), pressure waves within the sample generated as a result of the SSAW producing particle manipulation. The sample may be a sample flow moving through a channel, the channel having a particle manipulation region over a portion of the substrate in which the SSAW exists.

An apparatus for three-dimensional particle manipulation of particles within a fluid sample comprises a substrate having a substrate surface, a surface acoustic wave generator, operable to generate a surface acoustic wave (SAW, such as a SSAW) within a SAW region of the substrate surface, a channel configured to receive the fluid sample, the channel having a particle manipulation portion proximate the SAW region of the substrate, the particle manipulation portion providing manipulated particles within the fluid sample when the SAW is generated. The substrate surface may form a wall of the channel, and the SAW region of the substrate may form a wall of the particle manipulation portion of the channel.

BRIEF DESCRIPTION OF THE DRAWINGS

FIG. 5B illustrates the trajectories of two particle types in a fluid flow in the working region of FIG. 5, with the SAW generators turned on;

FIG. 5E illustrates the trajectories of two particle types in a fluid flow in the outlet region of FIG. 5C, with the SAW generators turned on;

DETAILED DESCRIPTION OF THE INVENTION

Example apparatus and methods using a novel acoustic manipulation technique using surface acoustic waves (SAW), in particular standing surface acoustic waves (SSAW), allow fast and effective particle manipulation. Examples include apparatus and methods for microparticle manipulation inside a microfluidic channel. Example approaches are simple, fast, dilution-free, and can be used to focus virtually any microparticles, including both charged and uncharged particles. The transparency of the particle manipulation device makes it compatible with most optical characterization tools used in biology and medicine, allowing particle characterization by fluorescence and/or other optical techniques. A surface acoustic wave (such as a SSAW) can be used for manipulation of arbitrary particles, such as micro/nano particles, and for example particle focusing within a fluid flow, particle sorting or separation. Throughout this disclosure, reference is made to surface acoustic waves (SAWs). It should be understood that standing surface acoustic waves (SSAWs) are one type of SAW, and are preferred for some embodiments. However, the present invention is not limited to SSAWs, as other types of SAWs may be used for some versions. Some versions will be described as utilizing SSAWs, but further versions may use other types of SAWs. An example of another type of SAW is a traveling surface acoustic wave (TSAW).

A SAW-based technique localizes most of the acoustic energy on the surface of the substrate, and has little loss along the propagation line, lowering the power consumption and improving the uniformity of the standing waves. The SAW technique is compatible with standard soft lithography techniques, and can be used in a wide variety of on-chip biological/biochemical applications. In experimental examples, a standing surface acoustic wave (SSAW) manipulation technique was used with a microfluidic device using a PDMS channel fabricated by standard soft lithography, and the SSAW was directed at an oblique or tilted direction to the flow channel elongation direction and the flow channel.

Examples of the present invention provide a novel method to implement the high-efficiency separation of micro/nano particles and cells using angled or tilted surface acoustic waves on a single-layer planar microfluidic device fabricated using standard soft-lithography technique. Compared to currently existing technologies (e.g. bulk acoustic wave based separation, magnetic field based separation and electrokinetic separation), this technique provides a higher efficiency, significant simplification for device fabrication, less invasiveness, and reduction of cost. Systems include in a low cost, high efficiency, and portable separation system for many applications such as blood component separation, cell separation, particle separation, cells/particles medium exchange, cell enrichment, and other particle enrichment. Certain species or characteristics of particles, such as cells, may be physically separated from a common stream to give a plurality of exit streams, sorted by species or some characteristic. As used in examples herein, a particle may be a biological cell unless otherwise defined, but the term cell is sometimes used separately to emphasize biological applications.

To date, many methods capable of particle and cell separation in microfluidic systems, such as centrifugal methods, magnetic force, hydrodynamic force, dielectrophoretic (DEP), and bulk acoustic waves (BAW) have been developed. Particle separation is possible through standing surface acoustic wave (SSAW)-induced acoustophoresis in a microfluidic channel, with a separation efficiency of 85% achieved. An angled or tilted interdigital transducer (TIDT) based particle separation technique in accordance with the present invention has demonstrated a remarkable separation efficiency of 98% or higher.

Figures 1, 2:
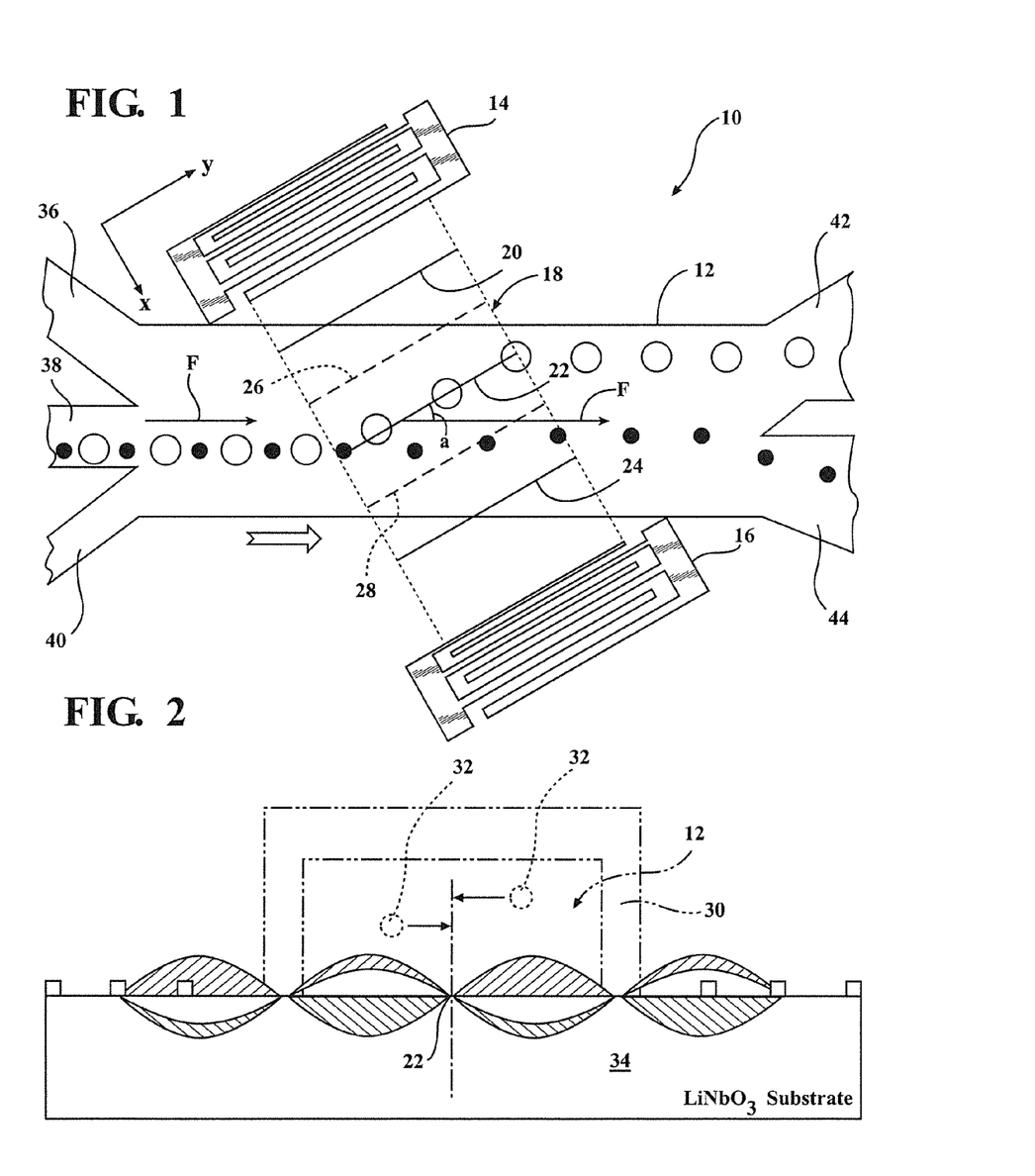
FIG. 1 is a schematic top view of a particle manipulation apparatus in accordance with the present invention.
FIG. 2 is a cross sectional schematic view showing the interaction of SSAWs with particles in a channel.

An exemplary apparatus for manipulating particles is shown at 10 in FIG. 1. A channel 12 is defined between a pair of spaced apart surface acoustic wave generators 14 and 16. The generators 14 and 16 together define a SSAW generator. In the illustrated example, the generators 14 and 16 are interdigitated transducers (IDTs). The surface acoustic waves from the generators 14 and 16 interact to form SSAWs therebetween. In FIG. 1, the SSAWS are indicated generally at 18, and have nodes indicated by solid lines at 20, 22 and 24 and anti-nodes indicated by dashed lines at 26 and 28. The central node is at 22. An SAW region may be considered to be the area where SSAWs are generated between the generators 14 and 16. The channel passes through the SAW region.

FIG. 2 is a cross sectional schematic view, taken along the central node 22. The channel 12 is defined inside a channel wall 30. The term "channel" may refer to the passage or the enclosing structure in this description. Particles 32 are shown being urged toward the antinode 22.

A fluid containing particles flows along the channel 12 in a flow direction indicated at F. This direction may also be considered a channel direction. The SSAWs may be said to have a SSAW direction, which lies along the line 22 in FIG. 1. That is, the SSAW direction is a direction aligned with the generally linear anti-nodes and nodes of the SSAWs. As shown, the SSAW direction is at an oblique angle to the flow direction or channel direction F. The SSAW direction is neither parallel to nor perpendicular to the flow and channel direction F. As known to those of skill in the art, oblique defines an angle between 0 and 90 degrees and between 90 and 180 degrees, not including 0, 90 or 180. As will be clear to those of skill in the art, SAWs other than SSAWs will also have nodes and anti-nodes, though they may be positioned differently than shown and may move over time. However, they will still occur at the angle indicated, with respect to the flow or channel direction F.

An example of a SSAW based separation device consists of a polydimethylsiloxane (PDMS) microfluidic channel 30 bonded in between an identical pair of IDTs deposited on a piezoelectric substrate 34. In FIG. 1, the microfluidic channel has three inlets 36, 38, and 40, and two outlets 42 and 44. The center inlet 38 introduces a fluid sample, containing particles to be manipulated, and the two side inlets introduce a buffer flow. In experimental arrangements, the pair of IDTs 14 and 16 were deposited in a parallel arrangement, and aligned at a specific oblique angle, a. Angles of 15°, 30°, and 45° to the channel and flow direction were used, but other oblique angles are possible. A RF signal was applied to each IDT to generate two identical SAWs. These two SAWs propagate in opposite directions and interfere with each other to form a standing SAW (SSAW) in between the IDTs where the PDMS microchannel 30 was bonded. Such a SSAW generates a parallel distribution of pressure nodes and antinodes on the surface of the substrate 34. The acoustic radiation force, generated from the pressure distribution, pushes the suspended particles towards pressure nodes or antinodes in the SSAW field, depending on the elastic properties of the microparticles. FIG. 2 shows how the particles are pushed towards the pressure node. Particles are injected through the center inlet channel 38 and hydrodynamically focused by two side flows from side inlets 36 and 40 before entering the SSAW field. Particles in this SSAW field experience lateral acoustic radiation force, drag force, gravity force and buoyant force. Gravity force and buoyant force are similar in magnitude but opposite in direction, and are almost balanced. The behavior of particles in the channel can be characterized by examining the drag force and acoustic radiation force.

The primary acoustic radiation force (Fr) and drag force (Fd) can be expressed as $$F_r = -\left(\frac{\pi p_o^2 V_p \beta_m}{2\lambda}\right) \Phi(\beta, \rho) \sin(2kx), \quad (1)$$

$$\Phi(\beta, \rho) = \frac{5\rho_p - 2\rho_m}{2\rho_p + \rho_m} - \frac{\beta_p}{\beta_m}, \quad (2)$$

$$F_d = -6\pi \eta r v), \quad (3)$$

where $\rho_0$, $\lambda$, $V_p$, $\rho_p$, $\rho_m$, $\beta_p$, $\beta_m$, $\eta$, r, and v are the acoustic pressure, wavelength, volume of the particle, density of the particle, density of the medium, compressibility of the particle, compressibility of the medium, medium viscosity, particle radius, and relative velocity, respectively. Equation (2) describes the acoustic contrast factor, $\phi$, which determines whether the particles move to pressure nodes or antinodes: the particles will aggregate at pressure nodes when $\phi$ is positive and pressure antinodes when $\phi$ is negative. It is believed that most particles and cells have positive $\phi$, and go to pressure nodes in the SSAW fields, bubbles and lipids usually have negative $\phi$ and move to pressure antinodes. Equations (1) and (3) indicate that the radiation acoustic force is proportional to the volume of the particle/cell while the drag force is proportional to the radius of particle. Large particles that experience larger acoustic force will be confined in the pressure node, and will be repositioned with large lateral displacements along the width of the channel. FIG. 1 shows larger particles being repositioned so as to alight with the pressure node 22. These larger particles are collected in upper outlet channel 42. For the small particles, the forces acting on them are not large enough to confine them in the pressure node. Therefore, they remain in the center stream by the drag force and are collected in the bottom outlet channel 44, as shown in FIG. 2.

Figure 3A:
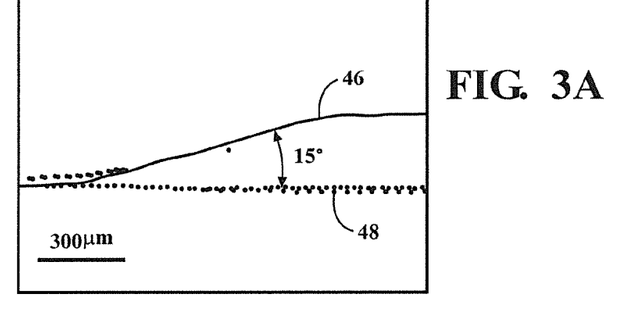
FIGS. 3A-3C illustrate the trajectories taken by two different particle types in the presence of SSAWs disposed at an oblique angle of 15, 30 and 45 degrees, respectively, to the direction of flow.
Figure 3B:
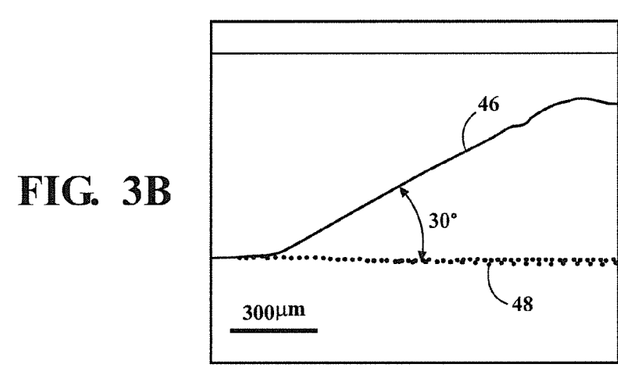
Figure 3C:
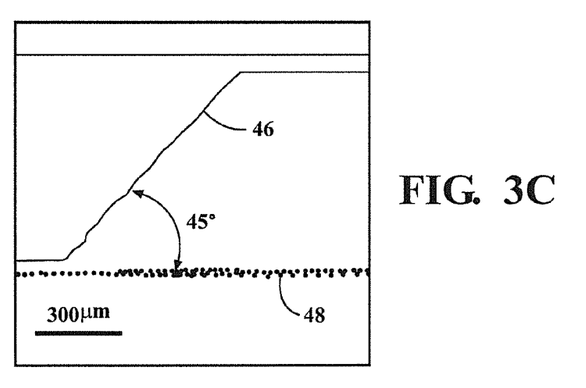

FIGS. 3A-3C illustrate the trajectories taken by 15 μm and 7 μm polystyrene particles in the presence of SSAWs disposed at an oblique angle of 15, 30 and 45 degrees, respectively, to the direction of flow. The solid-looking line at 46 represents the larger particles while 48 indicates the flow of smaller particles in each Figure.

Figure 4A:
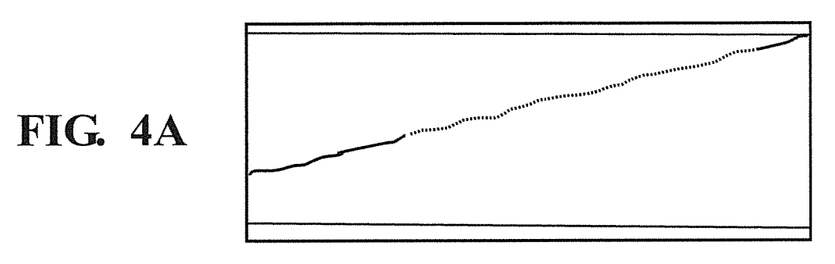
FIGS. 4A-4C illustrate the trajectories taken by a particle in the presence of SSAWs having three different input power levels.
Figure 4B:
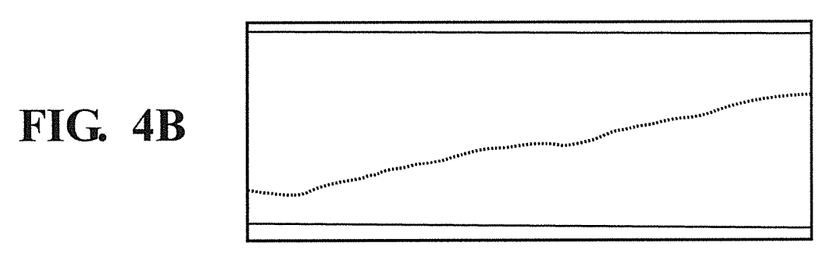
Figure 4C:
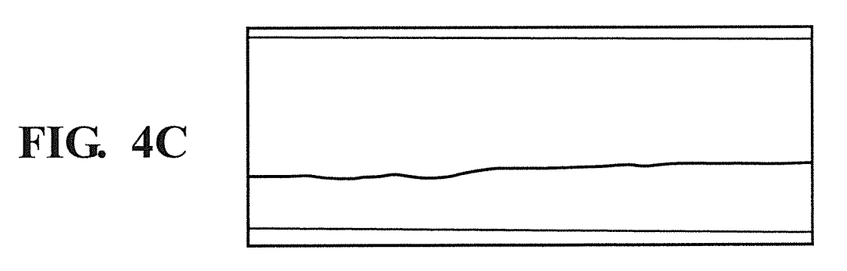

At a high input power, corresponding to large SSAW amplitude, acoustic radiation forces dominate and confine the particle trajectory along the angled pressure node, such as 22 in FIG. 1, achieving a large distance shift across the width of the channel. Low input power leads to small acoustic radiation forces and drag force dominates on the particles, causing a small lateral distance shift. The trajectory of 15 μm particles at different SSAW amplitude was experimentally recorded at a flow velocity of ~2 mm/s, as shown in FIGS. 4A-4C. FIG. 4A represents an input power of 27 dBm, FIG. 4B represents an input power of 23 dBm, and FIG. 4C represents an input power of 15 dBm. Since the acoustic radiation force depends on the mechanical properties such as volume, compressibility, and density, particles with differences in those properties can be differentiated and separated by the acoustic device described herein.

Figure 5:
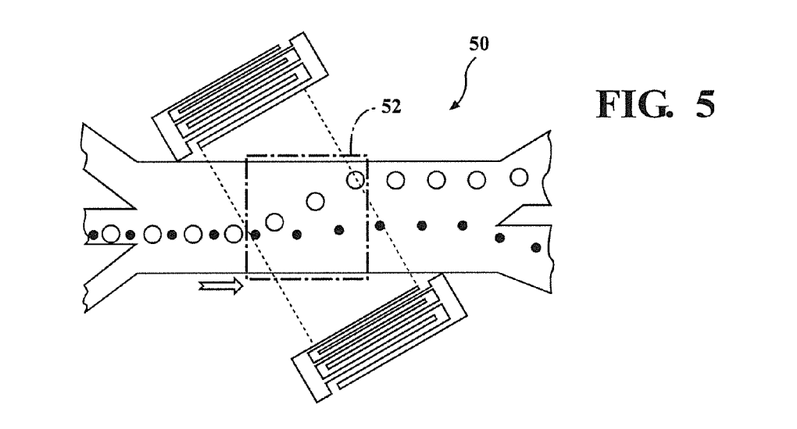
FIG. 5 is a schematic view similar to FIG. 1, with a working region indicated in dot-dash lines.
Figure 5A:
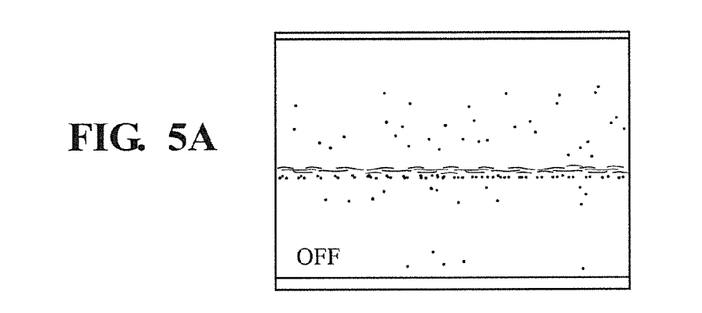
FIG. 5A illustrates the trajectories of two particle types in a fluid flow in the working region of FIG. 5, with the SAW generators turned off.
Figure 5B:
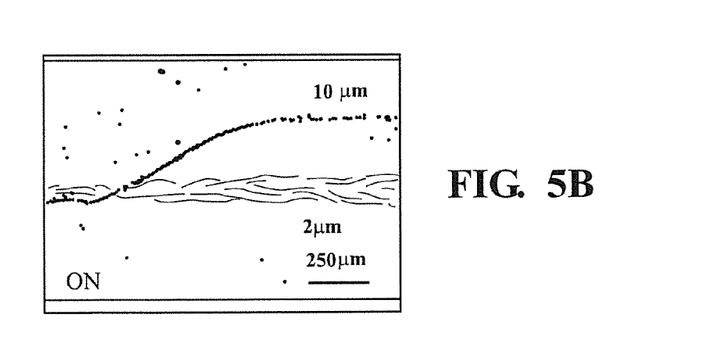
Figure 5C:
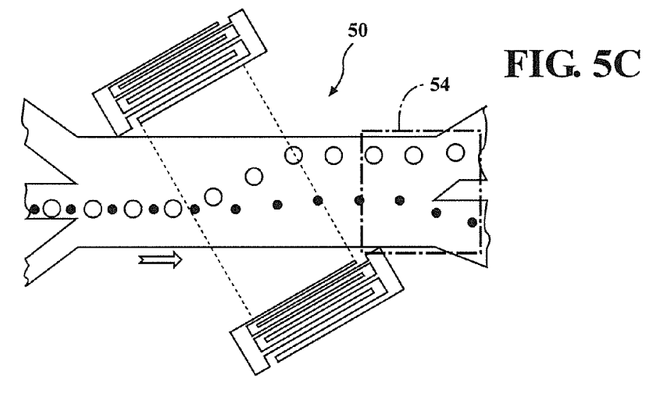
FIG. 5C is a schematic view similar to FIG. 5A, with an outlet region indicated in dot-dash lines.
Figure 5D:
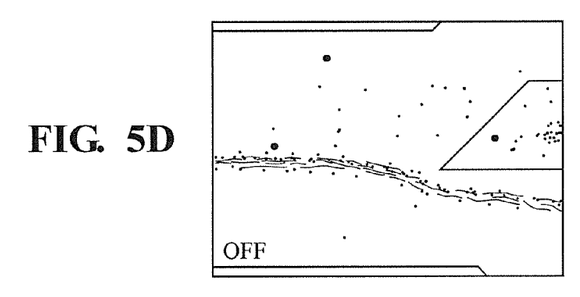
FIG. 5D illustrates the trajectories of two particle types in a fluid flow in the outlet region of FIG. 5C, with the SAW generators turned off.
Figure 5E:
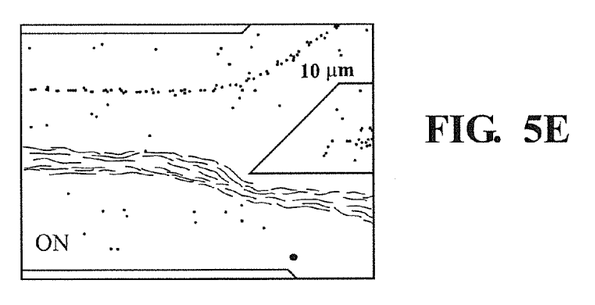
Figure 6:
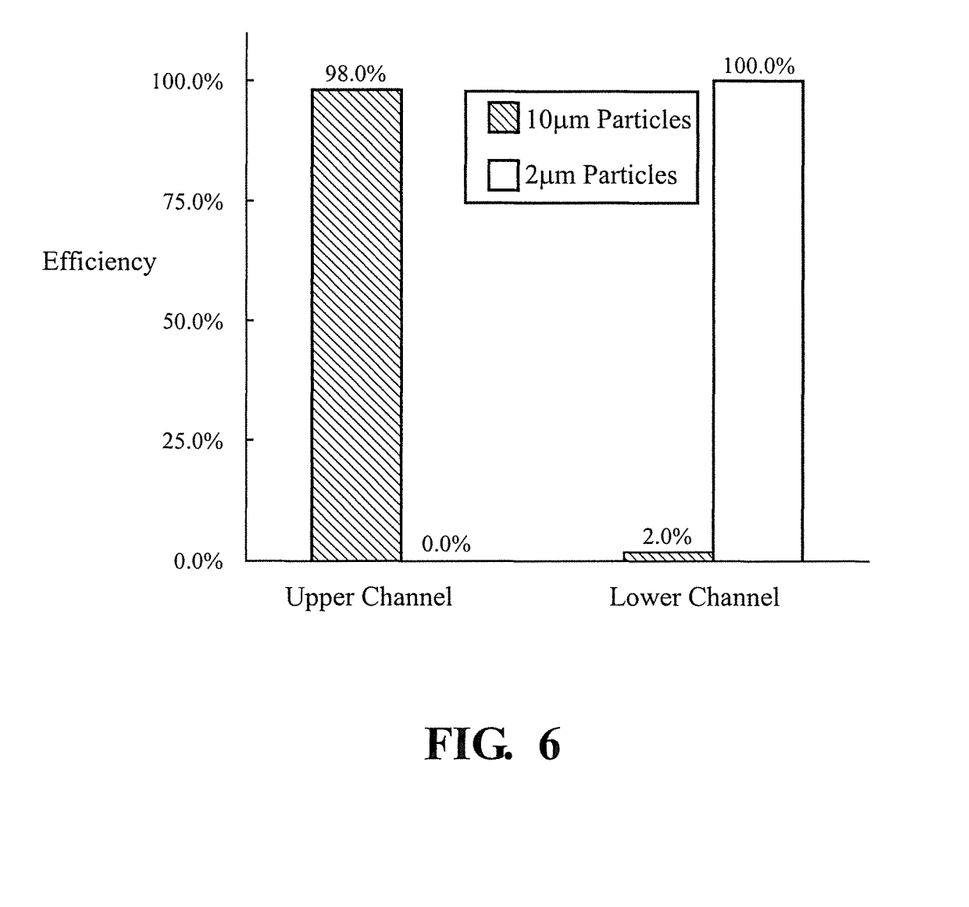
FIG. 6 is a graph presenting experimental data on the separation efficiency of the present invention.

An embodiment of the present invention was tested using polystyrene beads. Positions in the SAW working region and outlet of the channel were recorded to analyze the distribution of the particles, as shown in FIGS. 5-5E. FIG. 5 shows the device 50 with a working region indicated in dot-dashed lines at 52. A mixture of 10 μm and 2 μm particles were injected into the channel and were hydrodynamically focused in the center of the channel by two side flows. FIG. 5C shows the device and an outlet region at 54. When generators were turned off, small particles and big particles were flowing together along the stream and exited through the lower outlet channel, as shown in FIGS. 5A and 5D. When the generators were turned on, particles entering the working region 52 experienced acoustic radiation force, which pushed them towards the linear pressure nodes tilted with an angle of 30° with respect to the flow direction. At a flow velocity of 6.5 mm/s and input power of 16-23 dBm, the acoustic radiation forces pushed large particles towards the pressure node and confined them along the angled linear node until those particles exited the working region, as shown in FIG. 5B. The small particles, however, due to the insufficient acoustic radiation force acting on them, remained in the original flow stream. FIGS. 5B and 5E indicate that large particles were pulled out from the mixture stream and were separated through the upper outlet channel while small particles trajectory were not significantly affected and were collected in the lower outlet channel. The ratio of large and small particles collected from each outlet channel was analyzed to evaluate this method. The number of particles was counted through a recorded video. 98% of the large particles migrated to the upper outlet channel while 100% of the small particles remained in the lower outlet channel, as shown in FIG. 6.

To further examine the resolution of the technique, fluorescent polystyrene beads with diameters of 9.9 μm and 7.3 μm were mixed into an aqueous buffer. A mixture of those beads were injected into the device and set to flow at ~1.5 mm/s. The small beads and large beads were mixed before entering the SSAW working region. The large beads were extracted from the small beads stream while passing through the working region. The fluorescent intensity profile was scanned near the outlet channel to indicate the beads distribution. The results showed two peaks for small beads, which was caused by the non-uniform flow velocity distribution in the vertical direction. This is attributable to the hydrodynamic effect within the laminar flow. The experimental result shows that this method achieved the separation resolution of 30%, which is better than most of other methods.

Figure 7:
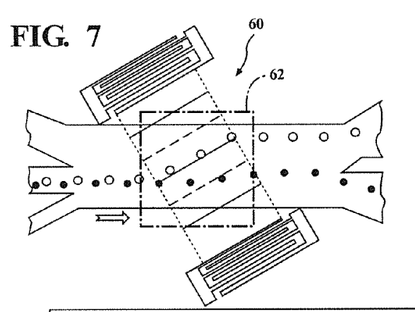
FIG. 7 is a schematic view similar to FIG. 1, with a working region indicated in dot-dash lines.
Figure 7A:
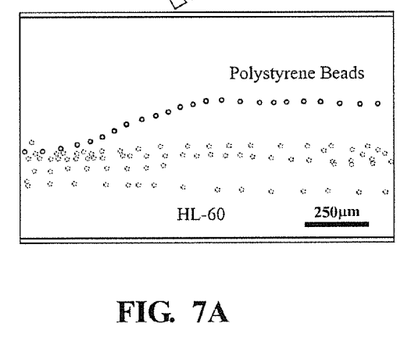
FIG. 7A illustrates the trajectories of two particle types in a fluid flow in the working region of FIG. 7, in the presence of SSAWs.
Figure 7B:
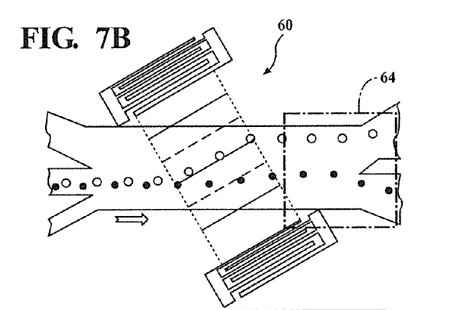
FIG. 7B is a schematic view similar to FIG. 7, with an outlet region indicated in dot-dash lines.
Figure 7C:
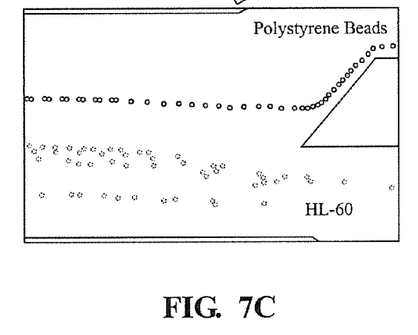
FIG. 7C illustrates the trajectories of two particle types in a fluid flow in the outlet region of FIG. 7B, in the presence of SSAWs.

To further explore the versatility of the inventive method, particle separation was carried out based on the difference of compressibility. HL-60 are a human promyelocytic leukemia cell line, with a diameter of ~15 μm. H1-60 cells (with a density of ~1.075 kg m$^{-3}$, compressibility of ~$4*10^{-10}$ Pa$^{-1}$) were mixed with 15 μm polystyrene beads (with a density of 1.05 kg m$^{-3}$, compressibility of ~$2.16*10^{-10}$ Pa$^{-1}$). These particles have similar sizes and densities but different compressibilities. FIGS. 7-7C show the separation of particles with different compressibilities. FIGS. 7 and 7B show an exemplary device 60 with a working region at 62 and an outlet region at 64. FIGS. 7A and 7C shown the separation in the working region and outlet region, respectively. Polystyrene beads (dark circles) were pulled out of HL-60 cells (dotted circles) in the SSAW working region and eventually collected by upper outlet channel.

Figure 8:
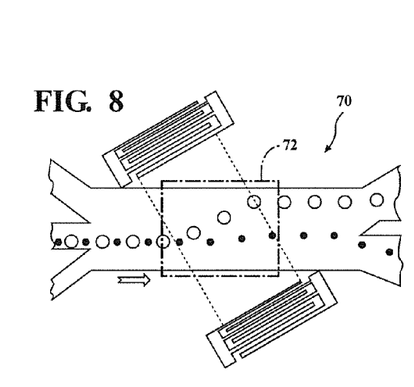
FIG. 8 is a schematic view similar to FIG. 1, with a working region indicated in dot-dash lines.
Figure 8A:
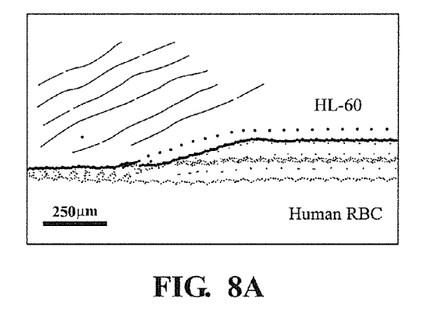
FIG. 8A illustrates the trajectories of two particle types in a fluid flow in the working region of FIG. 8, in the presence of SSAWs.
Figure 8B:
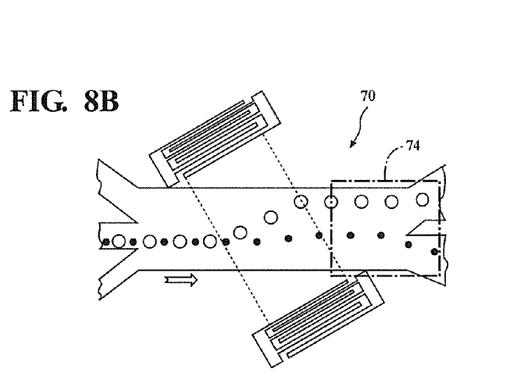
FIG. 8B is a schematic view similar to FIG. 8, with an outlet region indicated in dot-dash lines.
Figure 8C:
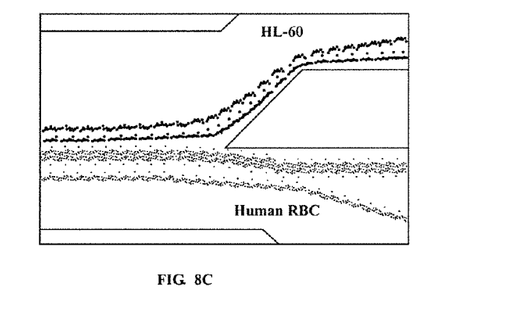
FIG. 8C illustrates the trajectories of two particle types in a fluid flow in the outlet region of FIG. 8B, in the presence of SSAWs.

To demonstrate the ability of the inventive device for biological applications, an experimental separation of human leukemia cancer cells from human blood was carried out. Human red blood cells (purchased from Zen-bio) were diluted with PBS (Phosphate buffered saline) buffer by 100 times and mixed with HL-60 (human promyelocytic leukemia cells). The ratio of blood cells and HL-60 was close to 1 to 1. FIGS. 8-8C represent stacked images showing the cell separation process, in which HL-60 cells were selectively moved from the red blood cells and collected from the upper outlet channel. FIGS. 8 and 8B show an exemplary device 70 with a working region shown at 72 and an outlet region shown at 74. FIGS. 8A and 8C shown the separation in the working region and the outlet region, respectively. To evaluate the separation efficiency, cells were collected by each outlet channel and then characterized using commercial standard flow cytometry (Coulter FC 500). As a comparison, the mixture sample was also counted through the flow cytometry. The results show that 82% of the cells from upper outlet channel were HL-60 and 81% were red blood cells from the lower outlet channel.

Circulating tumor cells (CTCs) have drawn increasing research attention in recent years due to their potential value in cancer prognosis, therapy monitoring, and metastasis research. Rare CTCs in the blood of patients with metastatic cancer are a potentially accessible source for detection, characterization, and monitoring of non-hematological cancers. The isolation of CTCs is a tremendous technical challenge due to their low concentration, as few as one cell per 10$^9$ haematological cells in blood.

To demonstrate the applicability of the present invention to CTC, the inventors studied isolation of cancer cells from human blood. In the study, 1 mL human whole blood was lysed using RBC Lysis Buffer [eBioscience], and the white blood cells (WBC) concentration was measured to be 2-4*106/mL. This erythrocyte-lysed blood sample was then mixed with 100 uL cancer cell (6*106/mL) to achieve a cancer cell concentration of 10%. Here MCF-7 cells (human breast cancer cell line) were used as a cancer cell model. The mixed sample was then delivered into a SSAW-based CTC isolation device through a syringe pump. Since cancer cells are usually much larger than white blood cells, when the cells entered the SSAW working region, cancer cells were isolated from WBCs. CTC cells and leukocytes are eventually collected from different outlets for consecutive characterization. EpCAM, CD45 surface markers (green), and a nuclear stain (DAPI, blue) were used to investigate the purity of isolated CTC. Epithelia cancer cells such as MCF-7 are positive to EpCAM (red), negative to CD45, and positive to DAPI (blue), while leukocytes are negative to EpCAM, positive to CD45, and positive to DAPI (blue). To evaluate the performance of cancer cell isolation using the inventive device, the recovery rate and purity of cancer cell isolation were investigated. The recovery rate (%) and purity (%) of cell isolation are defined as the percentage of the isolated cancer cell number over the spiked cancer cell number and that of the isolated cancer cell number over the total collected cell number, respectively. The MCF-7 cell line was used as the CTC model, and the preliminary result indicated a purity as high as 98%, much higher than that of the current commercial approach, Cellsearch (0.1%), and higher than that of other state-of-art label free CTC isolation methods (80%-90%).

Biocompatibility of the inventive CTC isolation device is very important since further CTC cell physiological studies will be conducted after CTCs are collected. Therefore, it is required for the isolation process to have very little, if any, physiological impact on the cells. To demonstrate the biocompatibility of the inventive device, cells viability, apoptosis, and proliferation assays were performed after exposure to an SAW field at a working power level (25 dbm, or 2 W/cm2). The WST-1 cell viability test (Roche), BrdU Cell Proliferation ELISA (Roche), and Calcein AM and SYTOX Orange (Invitrogen) were used to test cells viability, proliferation, and apoptosis, respectively. MCF-7 cells were delivered into the separation device at a flow rate of 2 uL/min under the input power of 25 dBm (2 W/cm2). Cell tests were then conducted immediately after being collected from the outlet. The results indicate that no significant changes were found in cell viability, apoptosis and proliferation. These promising results show that the inventive SAW device is ideal for CTCs isolation from blood for consecutive CTCs study without affecting cell physiological properties.

Fresh human whole blood with Acid Citrate Dextrose (ACD) as anticoagulant was purchased from Zen-bio. To lyse the red blood cells, 1 ml of whole blood was incubated with 10 ml of 1×RBC Lysis Buffer (eBioscience) for 10-15 min at room temperature followed by centrifugation at 400×g, resuspension in PBS, and cell counting with Hemacytometer to determine white blood cell (WBC) concentration. Then cultured MCF7 breast cancer cells were spiked into the prepared WBC suspension at a desired ratio. This prepared sample was injected into the inventive SSAW device for MCF7 separation.

After separation, cells from the CTC outlet were collected and fixed with 4% paraformaldehyde (Santa Cruz Biotechnology, Inc.) for 5 min and subsequently permeabilized with 0.2% Triton X-100 (Sigma-Aldrich) in PBS. These fixed cells were then stained with DAPI (nuclei staining), FITC-conjugated anti-CD45 antibody (WBC staining) (Invitrogen), and Phycoerythrin (PE)-conjugated anti-EpCAM antibody (MCF7 staining) (eBioscience). The stained cells were analyzed through epifluorescence imaging.

The present invention provides a unique cell separation microfluidic device using standing surface acoustic wave. Particles of varying size and compressibility can be effectively and continuously separated using this device. The inventors have successfully demonstrated on-chip continuous separation of 1) polystyrene beads with different size, 2) beads and cells with same size but different compressibility, 3) Leukemia cancer cells from human red blood cells, and 4) Human breast cancer cells from Human white blood cells as CTCs model. A series of cells viability, proliferation, and apoptosis tests were performed to prove excellent biocompatibility of the inventive method. In addition, the inventive SSAW device is simple, low cost, miniaturized, and can be fabricated via standard microfabrication, allowing the easy integration into other lab-on-chip technologies.

Examples of the invention provide novel apparatus and methods to implement the high-efficiency separation of micro/nano particles and cells using oblique angled standing surface acoustic waves on a single-layer planar microfluidic device fabricated using standard soft-lithography technique. Compared to currently existing technologies (e.g. bulk acoustic wave based separation, magnetic field based separation and electrokinetic separation), this technique provides a higher efficiency, significant simplification for device fabrication, less invasiveness, and reduction of cost. Examples of the novel system include low cost, high efficiency, and portable separation system for many applications such as blood/cell/particle separation, cells/particles medium exchange, and cells/particles enrichment.

An example apparatus for manipulating (sorting, separating, focusing, or otherwise manipulating) particles within a fluid sample includes a substrate, having a substrate surface; and an acoustic transducer such as an IDT, operable to generate an e.g. standing surface acoustic wave (SSAW) within a region of the substrate surface. A channel is configured to receive a fluid sample. For example, the channel may be a flow channel configured to receive a fluid sample having a flow direction. The flow direction may be at an oblique angle to the SSAW direction, e.g. at least 5 degrees from parallel or perpendicular to the flow direction, for example at least 10 degrees from parallel or perpendicular to the flow direction. For example, the angle between the SSAW and the channel direction may be between 5 and 85, such as between 10° and 80°, for example between 10° and 70°. These angular ranges are exemplary and not limiting. The SSAW generator may include a pair of spaced apart surface acoustic wave generators, and the surface acoustic wave generators may each be an interdigitated transducer (IDT) including interdigitated electrodes supported by the substrate. The substrate may be, or include, a piezoelectric substrate. The SAWs generated by the pair of transducers may be parallel to each other, with opposed direction, to form a SSAW extending between the transducers and at an oblique direction to the flow channel. A flow channel passes between the transducers and proximate an SSAW formed between them. Differing pressure forces on different particle types may be used to form a plurality of output particle streams downstream from the SSAW region. These output particle streams may then be collected by a plurality of output channels, each output channels collecting a stream of particular particle type.

An example apparatus may be a microfluidic device, the channel being a microchannel having at least one cross-sectional dimension less than 1 mm, the particles being microparticles having a cross-sectional dimension less than 100 microns. An apparatus may further include a particle characterization device, operable to characterize manipulated particles.

An example apparatus may be or further include a cytometer, fluorescence particle detector, particle sorter, fluorescent spectrometer, genetic analyzer, chromatograph, electrophoresis-based detector, biomarker detector, blood fractionator, or blood plasma fractionator. Example apparatus include portable, point-of-care microfluidic diagnostic apparatus for medical use. Blood separation can be used to assist diagnostics of diseases through improved detection of clinical markers, such detection of blood components such as protein components.

An example apparatus for manipulating particles within a fluid sample, for example separating particles having different characteristics, includes a substrate supporting a pair of spaced-apart surface acoustic wave transducers configured to generate a standing surface acoustic wave (SSAW) within a SSAW substrate region located between the transducers, and a channel configured to receive a fluid flow including particles, the channel having a SSAW region where the channel has a SSAW channel region where the channel passes proximate or adjacent the SSAW substrate region. The substrate may form a wall of the channel, or the channel may be bonded to the substrate within the SSAW substrate region. The SSAW has an SSAW direction at an oblique angle to the channel direction. In this context, the SSAW direction is a direction parallel to linear nodes of the SSAWs. The apparatus is operable to sort particles within the fluid sample when the fluid sample is introduced into the channel and the SSAW is generated. Pressure nodes and antinodes are generated perpendicular to a line between the generators. Particles may be selectively directed to nodes or antinodes, depending on particle properties. The physical separation of the particle streams may be controlled through the flow direction, angle of the SSAW to the channel, flow speed, and/or other control parameters. The physical separation may be matched to the separation of a pair of output channels, so that particles directed to pressure nodes exit through one outlet channel, and particles not directed to nodes or directed to anti-nodes exit through the other outlet channel.

An example device includes a pair of interdigital transducers (IDTs, also referred to as interdigitated transducers) supported by a piezoelectric substrate. An IDT may comprise two interlocking comb-shaped electrodes, the electrodes being provided by a metal or other conducting coatings supported by the substrate. The piezoelectric substrate may comprise a ferroelectric material such as lithium niobate, and the IDTs may be deposited on a lithium niobate substrate.

Particle suspensions (such as microparticle and/or nanoparticle suspensions) are introduced through a channel located between two IDTs. The channel may be formed in a polymer, such as PDMS. For example, the channel may be formed by a molded polymer element on the substrate, and may be a microchannel. The molded polymer element may additionally include a cut-out (area in which it does not contact the substrate) so as to define the SSAW region of the substrate. A radio-frequency signal is applied to each IDT, which then generates a SAW that propagates toward the channel. The interference of the SAWs results in the formation of a SSAW on the substrate.

An example particle manipulation apparatus comprises a substrate, at least one surface acoustic wave (SAW) generator operable to generate a standing surface acoustic wave (SSAW) in the substrate; and a channel configured to receive a fluid sample including particles, the channel having a particle manipulation region located on a portion of the substrate in which the SSAW is generated. Methods and apparatus according to embodiments of the present invention may further include particle characterization, for example using radiation directed at a manipulated particle flow, or manipulated particles within a static fluid sample.

In another example, a particle manipulation apparatus or method in accordance with the present invention utilizes other forms of acoustic waves, such as bulk acoustic waves, wherein the waves are at an oblique angle to the channel and/or flow direction. In any of the embodiments discussed herein, other types of acoustic waves may be substituted for the surface acoustic waves described.

Particle characterization may include apparatus and methods for particle detection, particle analysis, particle counting, and combinations of such approaches. For example, a radiation source may be used to direct radiation towards manipulated particles within a fluid medium. The integration of particle manipulation with analytical methods and apparatus allows improved methods and apparatus for particle characterization. Particles may be suspended in the fluid medium, which may be a sample flow through the channel.

For example, the integration of microfluidics devices with single microparticle detection techniques allows improved microparticle characterization. Examples of the present invention include apparatus and methods for flow cytometry, and apparatus for counting, analysis, and sorting of microparticles in a sample flow. Microparticles may be defined as particles having a dimension of less than 1 mm, in particular less than 500 microns, and more particularly less than 100 microns. Microparticles may include cells, molecules, biomolecules, and the like.

Examples of the present invention include improved flow cytometers and other cell characterization devices, improved molecule detection devices, other analyte characterization devices, analyte sorting devices, genetic analysis devices, and the like. A SAW (SSAW or propagating SAW) can be used for dynamic particle separation and subsequent sorting. A particle may be a molecule (such as a polymer, macromolecule, or biomolecule), biological structure (such as a cell, for example a blood cell), particle (of any type), micelle, droplet of different density from a host fluid, and the like.

Apparatus and methods in accordance with the present invention may be used for a wide variety of applications. The apparatus and method may be used in almost all applications in which different components have a difference in size or density or mechanical properties. Some non-limiting examples include: separation of different components (red blood cells, white blood cells, platelets, plasma, etc) of a blood sample; separation of circulating tumor cells from a blood sample; separation of circulating endothelial cells from a blood sample; separation of protein biomarker bound particles from a blood sample; separation of microvesicles/exosomes bound particles from a blood sample; separation of fetal nucleated erythrocytes from a maternal blood sample (based on size and deformability); stem cell isolation based on size differences; and bacteria enrichment from a blood sample. Other applications will be clear to those of skill in the art.

An apparatus may be a planar microfluidic device. A channel may have a lower wall parallel to and proximate the substrate, opposed side walls, and an upper wall. A channel width and/or height may be in the range 100 nm-1 mm, for example in the range 1 micron-500 microns. Other dimensions are possible.

A piezoelectric substrate may comprise lithium niobate, lithium tantalate, lead zirconium titanate, polymer such as polyvinylidene fluoride (PVdF) or other fluoropolymer, quartz, or other material. An IDT can also form part of a sensor system, for example using time gating or monitoring drive signal properties. In some examples, the substrate may provide a wall of the flow channel, or the flow channel may have a wall bonded to the substrate.

Patents, patent applications, or publications mentioned in this specification are incorporated herein by reference to the same extent as if each individual document was specifically and individually indicated to be incorporated by reference. In particular, the entire content of application Ser. No. 12/631,059, filed Dec. 4, 2009, is incorporated herein by reference.

The invention is not restricted to the illustrative examples described above. Examples are not intended as limitations on the scope of the invention. Methods, apparatus, compositions, and the like described herein are exemplary and not intended as limitations on the scope of the invention. Changes therein and other uses will occur to those skilled in the art. The scope of the invention is defined by the scope of the claims, including all equivalents.

The invention claimed is:

1. An apparatus for sorting particles within a fluid sample, the apparatus comprising:
   a substrate, having a substrate surface;
   a surface acoustic wave (SAW) generator configured to generate a SAW within a SAW region of the substrate surface, the SAW having a SAW direction aligned with a generally linear pressure node;
   a channel, configured to receive the fluid sample, the fluid sample having a flow direction, the flow direction being at an oblique angle to the SAW direction; and
   a plurality of output channels arranged and disposed to collect a plurality of output particle streams from the fluid sample in the channel.

2. The apparatus of claim 1, wherein:
   the SAW generator comprises a pair of spaced apart surface acoustic wave generators, the surface acoustic wave generators each being an interdigitated transducer including interdigitated electrodes supported by the substrate.

3. The apparatus of claim 1, wherein:
   the substrate is a piezoelectric substrate.

4. The apparatus of claim 1, wherein:
   the apparatus is a microfluidic device;
   the channel being a microchannel having at least one cross-sectional dimension less than 1 mm; and
   the particles being microparticles having a cross-sectional dimension less than 100 microns.

5. The apparatus of claim 1, wherein:
   the SAW generator is a standing surface acoustic wave (SSAW) generator configured to generate a SSAW within the SAW region.

6. An apparatus for sorting particles within a fluid sample, the apparatus comprising:
   a substrate;
   a first surface acoustic wave generator;
   a second surface acoustic wave generator, the first and second surface acoustic wave generators being configured to generate a surface acoustic wave (SAW) within a SAW region of the substrate, the SAW having a SAW direction aligned with a generally linear pressure node of the SAW;
   a channel configured to receive a fluid sample including particles, the channel having a sorting portion proximate the SAW region of the substrate, the channel having a channel direction; and a plurality of output channels arranged and disposed to collect a plurality of output particle streams from the fluid sample in the channel, wherein the SAW direction is disposed at an oblique angle to the channel direction, and wherein by the apparatus is configured to sort particles within the fluid sample into the plurality of output particle streams when the fluid sample is introduced into the channel and the SAW is generated.

7. The apparatus of claim 6, wherein:
the SAW generator is a standing surface acoustic wave (SSAW) generator configured to generate a SSAW within the SAW region.

8. The apparatus of claim 6, wherein:
the substrate is a piezoelectric substrate; and
the first and second surface acoustic wave generators each comprise electrodes supported by the substrate.

9. The apparatus of claim 6, wherein:
the substrate forms a wall of the channel.

10. The apparatus of claim 6, wherein:
the apparatus is a microfluidic device;
the channel is a microchannel; and
the microchannel has at least one cross-sectional dimension less than 1 mm.

11. The apparatus of claim 6, wherein:
the channel is a flow channel configured to receive a sample fluid flow.

12. The apparatus of claim 6, wherein:
the particles are microparticles having a diameter of less than 100 microns.

13. The apparatus of claim 12, wherein:
the microparticles include biomolecules or cells.

14. A method of sorting a plurality of different types of particles within a fluid sample including the plurality of different types of particles, the method comprising:

providing an apparatus for sorting particles within a fluid sample, the apparatus comprising:
  a substrate, having a substrate surface;
  a surface acoustic wave (SAW) generator;
  a channel, configured to receive the fluid sample; and
  a plurality of output channels;
introducing the fluid sample to the flow channel, the fluid sample including the plurality of different types of particles and having a flow direction;
generating a SAW within a SAW region of the substrate surface, the SAW having a SAW direction aligned with a generally linear pressure node, the flow direction being at an oblique angle to the SAW direction;
sorting the plurality of different types of particles into a plurality of output particle streams by type; and
sorting the plurality of output particle streams into the plurality of output channels by type.

15. The method of claim 14, wherein:
the generating a SAW step comprises generating a standing surface acoustic wave (SSAW).

16. The method of claim 14, wherein:
the fluid sample is a sample flow directed along the flow channel;
the flow channel is supported by the substrate;
the flow channel is a microchannel within a microfluidic device; and
the method further includes particle characterization, particle focusing, particle separation, particle fractionation, or particle selection.

17. The method of claim 14, wherein:
the fluid sample includes a first particle type being directed by pressure forces induced by the SAW and a second particle type not being directed by the pressure forces, so as to produce a first stream of the first particle type and a second stream of the second particle type.

* * * * *